(12) United States Patent
Garadi et al.

(10) Patent No.: US 10,548,576 B2
(45) Date of Patent: Feb. 4, 2020

(54) CONTROL FOR SURGICAL HANDPIECE

(71) Applicant: MEDTRONIC XOMED, INC., Jacksonville, FL (US)

(72) Inventors: Vikram Garadi, Fort Worth, TX (US); Manfred K. Luedi, Jacksonville, FL (US); Larry Dale Estes, North Richland Hills, TX (US)

(73) Assignee: Medtronic Xomed, Inc., Jacksonville, FL (US)

( * ) Notice: Subject to any disclaimer, the term of this patent is extended or adjusted under 35 U.S.C. 154(b) by 517 days.

(21) Appl. No.: 15/207,755

(22) Filed: Jul. 12, 2016

(65) Prior Publication Data

US 2018/0014820 A1    Jan. 18, 2018

(51) Int. Cl.
*A61B 17/00*    (2006.01)

(52) U.S. Cl.
CPC .... *A61B 17/00* (2013.01); *A61B 2017/00039* (2013.01); *A61B 2017/0046* (2013.01); *A61B 2017/00367* (2013.01); *A61B 2017/00424* (2013.01); *A61B 2017/00876* (2013.01)

(58) Field of Classification Search
CPC ...................... G01D 5/142–147; G01R 33/072
See application file for complete search history.

(56) References Cited

U.S. PATENT DOCUMENTS

| | | | |
|---|---|---|---|
| 6,090,123 A | 7/2000 | Culp et al. | |
| 6,752,816 B2 | 6/2004 | Culp et al. | |
| 8,197,501 B2 | 6/2012 | Shadeck et al. | |
| 8,956,342 B1 | 2/2015 | Russo et al. | |
| 2002/0087179 A1* | 7/2002 | Culp | A61B 17/1626 606/167 |
| 2002/0175789 A1 | 11/2002 | Pimouguet | |
| 2009/0240272 A1 | 9/2009 | Shadeck et al. | |
| 2012/0221028 A1* | 8/2012 | Shadeck | A61B 17/1622 606/167 |
| 2014/0276949 A1 | 9/2014 | Staunton et al. | |

OTHER PUBLICATIONS

International Search Report and Written Opinion of the International Searching Authority for PCT/US2017/037399, dated Aug. 31, 2017, 10 pages.

* cited by examiner

*Primary Examiner* — Carl H Layno
*Assistant Examiner* — Dacheng Xie
(74) *Attorney, Agent, or Firm* — Dicke, Billig & Czaja, PLLC

(57) ABSTRACT

A powered surgical handpiece including a housing, a printed circuit board, a sensor, and an actuator assembly. The housing has a longitudinal axis extending from a first end to a second end of the housing. The printed circuit board has a first face and a second opposing face. The first and second faces extend perpendicular to the longitudinal axis. The sensor is coupled to the first face of the printed circuit board. The sensor is centered along the longitudinal axis of the housing. The actuator assembly includes a lever and an actuator. The lever is pivotally coupled to the housing. The lever maintains a magnet slidably positionable along the lever. The magnet is positionable to be proximal to the sensors.

12 Claims, 4 Drawing Sheets

CONTROL FOR SURGICAL HANDPIECE

BACKGROUND

Surgical instruments use a variety of methods to control the operating speed of the instrument. For example, a powered surgical instrument may use a control lever that can be moved to increase or decrease the operating speed of the instrument. In other examples, a foot pedal may be used to increase or decrease the operating speed of the surgical instrument.

Some conventional powered surgical instruments include the control lever fixed to the instrument. The control lever may be resiliently and pivotally coupled to the instrument such that a user may pivot the control lever towards the instrument to increase the operating speed, and then allow the control lever to resiliently pivot away from the instrument to decrease the operating speed. The control lever may provide only limited adjustability of finger control positions for the surgeon, mostly predefined positions and not cover all ergonomic positions for ease of use and access to the surgical site. Some conventional powered surgical instruments include sensors positioned close to the perimeter of the housing and aligned with the housing to detect a magnetic field perpendicular to the housing to detect movement of the control lever in order to increase, decrease, or maintain the operating speed of the surgical instrument. Typically four sensors are disposed in the housing in order to detect the magnetic field when the control lever is positioned in one of the predefined positions. Alignment of the sensors within the housing in order to detect the perpendicular magnetic field of the magnet in the control lever can be difficult. The size of the surgical instrument must be large enough to accommodate all of the sensors in their aligned positions.

SUMMARY

One example provides a powered surgical handpiece including a housing, a printed circuit board, a sensor, and an actuator assembly. The housing has a longitudinal axis extending from a first end to a second end of the housing. The printed circuit board has a first face and a second opposing face. The first and second faces extend perpendicular to the longitudinal axis. The sensor is coupled to the first face of the printed circuit board. The sensor is centered along the longitudinal axis of the housing. The actuator assembly includes a lever and an actuator. The lever is pivotally coupled to the housing. The lever maintains a magnet slidably positionable along the lever. The magnet is positionable to be proximal to the sensors.

Another example provides a control for a powered surgical instrument. The control includes a housing having a central longitudinal axis, a sensor mounted to a printed circuit board within the housing along the central longitudinal axis, and an actuator assembly including a lever pivotally coupled to the housing. The lever includes a magnet. The lever is operable to move the magnet relative to the sensor in order to vary a signal that is produced by the sensor in response to a magnetic field of the magnet.

Another example provides a method of controlling a powered surgical instrument. The method includes pivoting a terminal end of a lever towards a housing and sliding a switch having an actuator coupled to the lever to a position proximal to a sensor centrally disposed within the housing. The actuator has a magnetic field parallel to a length of the lever. The method also includes sensing a magnetic field of the actuator with the sensor and activating a surgical implement coupled to the powered surgical instrument in response to the sensed magnetic field.

DETAILED DESCRIPTION

Figure 1:
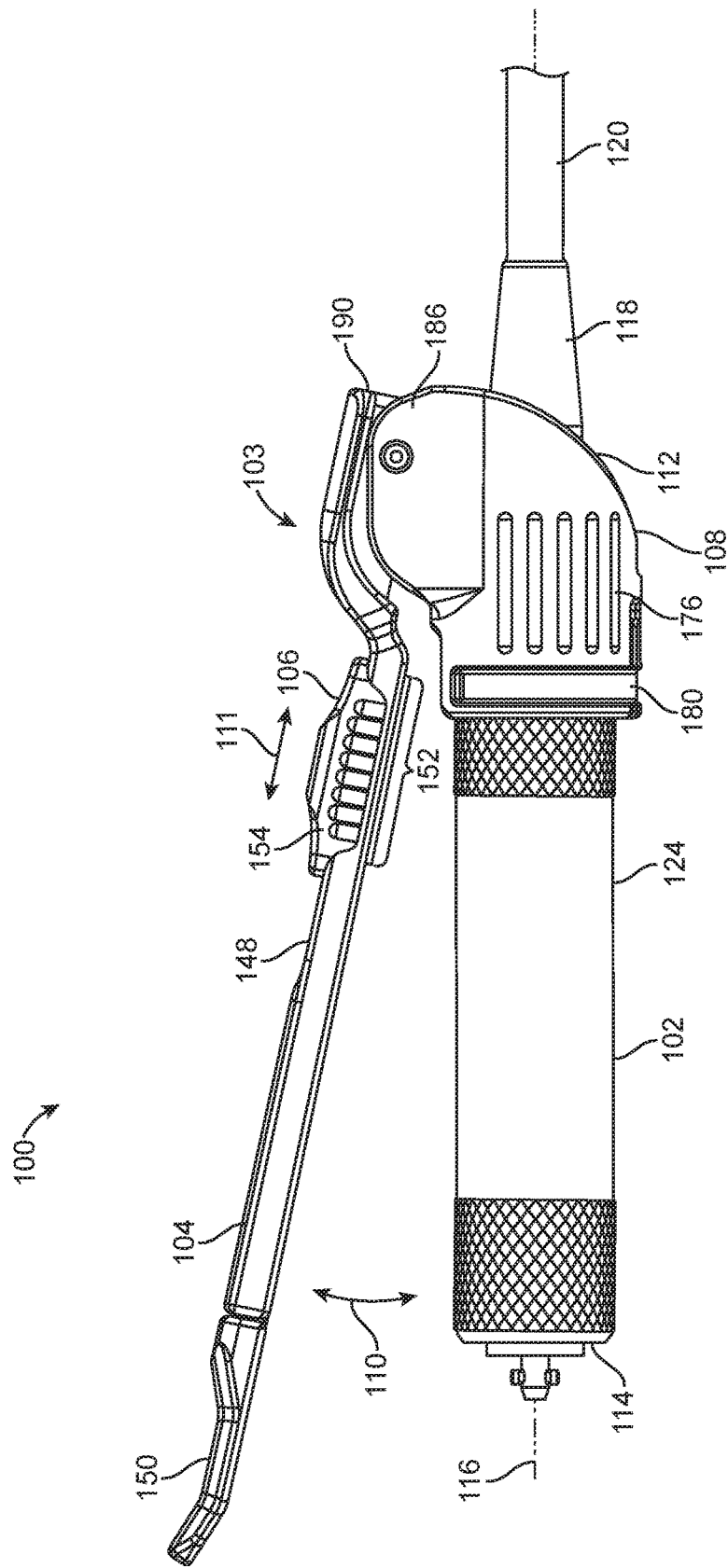
FIG. 1 is a perspective view illustrating an embodiment of a surgical instrument.

Some aspects in accordance with the present disclosure relate to surgical tools, and more particularly, to a control for use in powered surgical instruments. FIG. 1 illustrates one embodiment of a powered surgical instrument 100 in accordance with aspects of the present disclosure. The powered surgical instrument 100 includes a housing 102 and an actuator assembly 103. The actuator assembly 103 includes a lever 104, an actuator 106, and a collar 108. The lever 104 pivotally extends away from the housing 102 as indicated by arrow 110. The housing 102 and the lever 104 can be grasped in a single hand of a user. The actuator 106 is slidably coupled on the lever 104 as indicated by arrow 111. The housing 102 of the powered surgical instrument 100 is generally cylindrical and extends from a first end 112 to a second end 114 along a central longitudinal axis 116. The first end 112 includes a back nut (see, e.g., FIG. 2) for attachment to a cable 120 used to provide power to the powered surgical instrument 100. A surgical implement (not shown) can be attached at the second end 114. The surgical implement can be a cutting tool, dissection tool, or other tool useful in a surgical procedure, for example.

The on/off operation and motor speed of the surgical instrument 100 is controlled by the actuator assembly 103 fitted around the outside of the housing 102. The actuator assembly 103 can be removably attached to the housing 102. The actuator assembly 103 includes the collar 108 that is removably fitted over the housing 102. The lever 104 is pivotally secured to the collar 108 to extend along a length of housing 102 toward the second end 114. The speed of operation of the surgical instrument 100 can be varied as corresponding to the position or proximity of the lever 104 to the housing 102, as discussed in more detail below.

Figure 2:
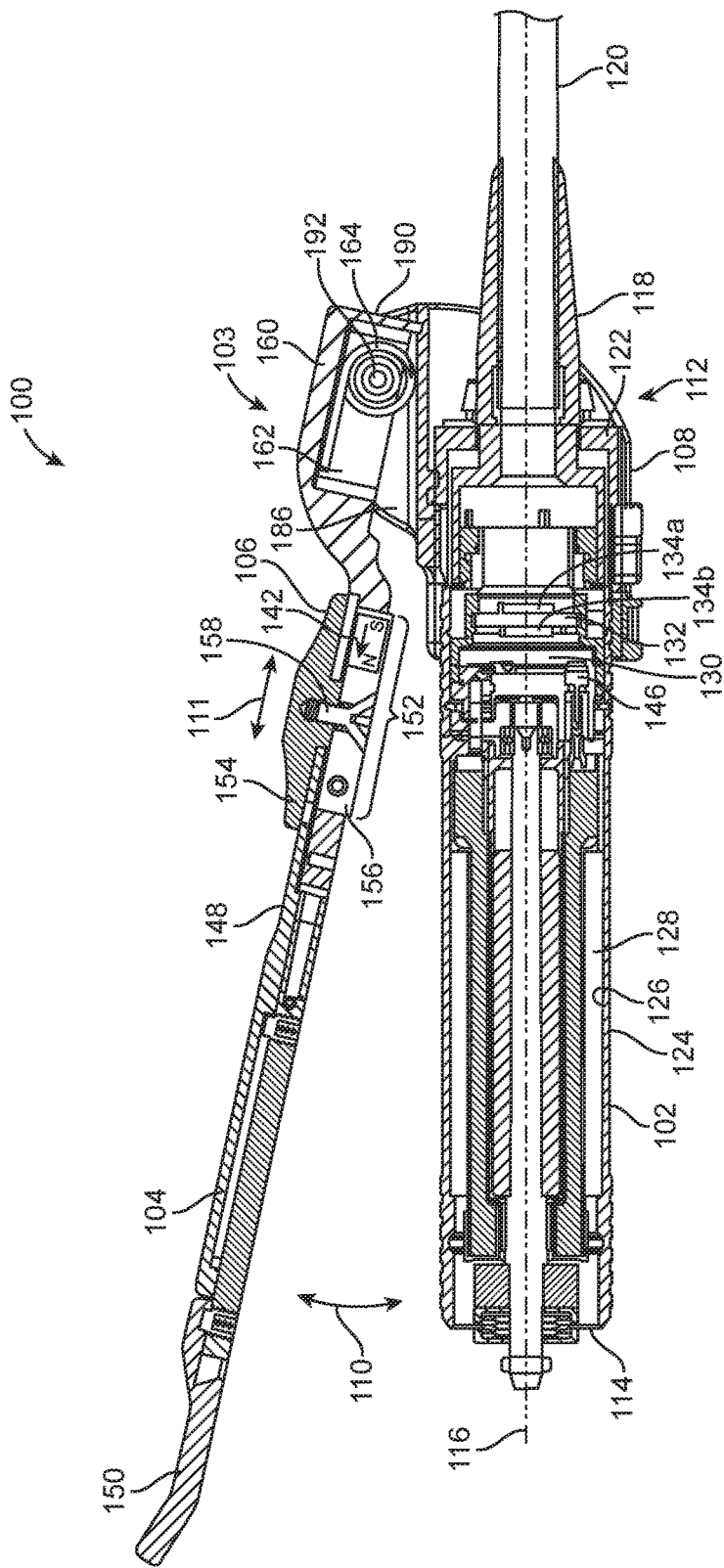
FIG. 2 is a cross-sectional view of the surgical instrument illustrated in FIG. 1.

With additional reference to FIG. 2, the housing 102 has an outer surface 124 and an inner surface 126 defining a housing volume 128. The housing volume 128 is suitable to contain a plurality of control components for the surgical instrument 100. The control components can include a connector insert 130, a board 132, and at least one sensor 134. The control components work in cooperation with the lever 104 and the actuator 106 of the actuation assembly 103, as described further below.

Figure 3:
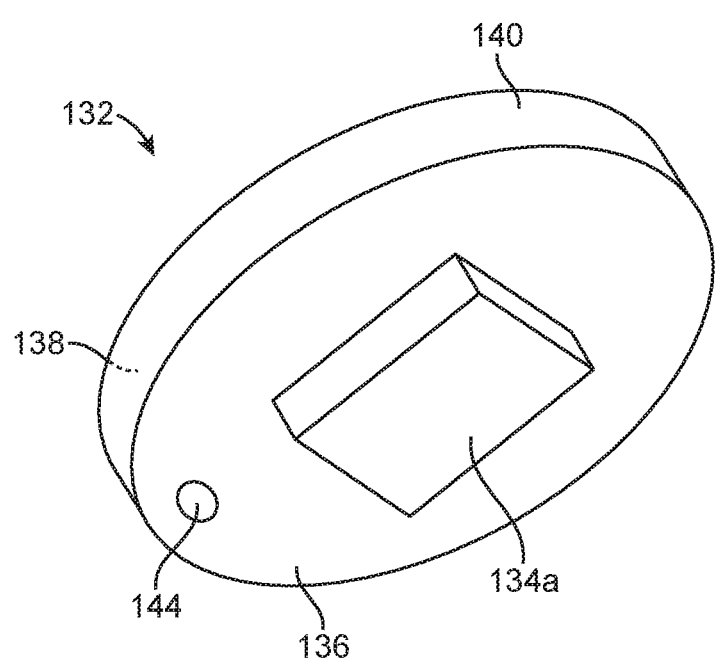
FIG. 3 is an exploded perspective view of an embodiment of a board with sensors used in the surgical instrument of FIG. 1.

Electrical cables or wiring extend within the housing 102, from the motor (and cable 120), to electrically connect and operate the surgical implement, such as a cutter (not shown). The electrical cables can include power and control cables. With additional reference to the board 132 illustrated in FIG. 3, the electrical cables, or wiring, can extend through an opening 144, provided in the printed circuit board 132 or in a space provided adjacent to the printed circuit board 132. In one embodiment, the cables can electrically connect from the motor to the surgical implement via a pin 146 extending through a connector insert, or opening, in the board 132. The pin 146 can be electrically conductive. The electrical wires coupled to the motor can be terminated directly at the board 132. For example, the electrical wires can include three wires, one for each phase of the motor (i.e., three-phase motor). Alternatively, the pin 146 interfaces with the board 132 without extending through the board 132. A contact block can hold the pin 146 (or pins 146) as part of the cables inserted into the housing 102. The wires can extend fully through the opening 144. The opening 144 can be positioned at the edge 140 of the board 132 or elsewhere as appropriate. In some embodiments, the pin 146 is coupled to a cable and inserted into a receptacle of a motor used to power the surgical implement. Regardless, the pin 146 can directly electrically connect to the printed circuit board 132.

The sensor(s) 134 are mounted on the board 132 disposed in the housing 102. The board 132 can be a printed circuit board (PCB) and can include circuitry and/or circuit board components known in the art. The board 132 can have a generally circular base having a first surface 136, a second surface 138 opposite the first surface 136, and an edge 140 extending between the first surface 136 and the second surface 138. Within the housing 102, the first surface 136 and the second surface 138 are disposed to extend perpendicular to the longitudinal axis 116. In one embodiment, the sensor(s) 134 include a first sensor 134a and a second sensor 134b with the first sensor 134a disposed on the first surface 136 of the board 132 and the second sensor 134b disposed on the second surface 138 of the board 132. The first and second sensors 134a, 134b are centered on the board 132 and with respect to the central longitudinal axis 116. The circuit board 132 is disposed within the housing 102 in a location that the sensors 134 can sense, or detect, an axial component of the magnetic field of the magnet 142. The sensor(s) 134 can detect the same magnetic field regardless of the circumferential position of the actuator 106. In one embodiment, the sensor 134a is employed to provide a "run" mode for variable speed control of the rotation of the motor and attached surgical implement and the second sensor 134b can be employed to detect axial movement of the magnet 142 for deactivation of the lever 104 during non-use of the surgical instrument, for example, for safety. The sensor(s) 134 can be Hall Effect sensors or other appropriate sensor, for example. The sensor(s) 134 monitor the position of a magnet 142 internal to the actuator 106 when the actuator assembly 103 is used to control the on/off state and the speed of the motor (not shown).

The centrally disposed sensor(s) 134 can receive magnetic field information from the actuator 106 regardless of the rotational position of the lever 104 around the circumference of the housing 102. The sensor(s) 134 interface with the magnet 142 of the actuator 106. The magnet 142, of the actuator 106 is fitted in the lever 104. The position of the magnet 142 is monitored by the sensor(s) 134 as an indication of the desired operating speed of the motor. As illustrated in FIG. 2, for example, the magnet 142 is positioned with the north-south polarity extending along a length of the lever 104, between the ends of the lever. The magnetic field axis direction of the magnet 142 is generally parallel to the housing 102 when the lever 104 is pivoted and pressed against the housing 102. Each of sensor(s) 134a, 134b is located coaxially with the longitudinal axis 146 on the printed circuit board 132. The sensor(s) 134 are aligned to receive only an axial component of the magnetic field generated by the actuator 154. In one embodiment, when a pair of sensors 134 is included, each sensor 134a, 134b of the pair of sensors is disposed on an opposite side 136, 138 of the printed circuit board 132. The board 132 and sensor(s) 134 are positioned such that the actuator 106 can be positioned perpendicular to the sensor(s) 134, and the magnetic field axis direction of the actuator 106 parallel to the longitudinal axis of the housing 102, as described further below.

Figure 4:
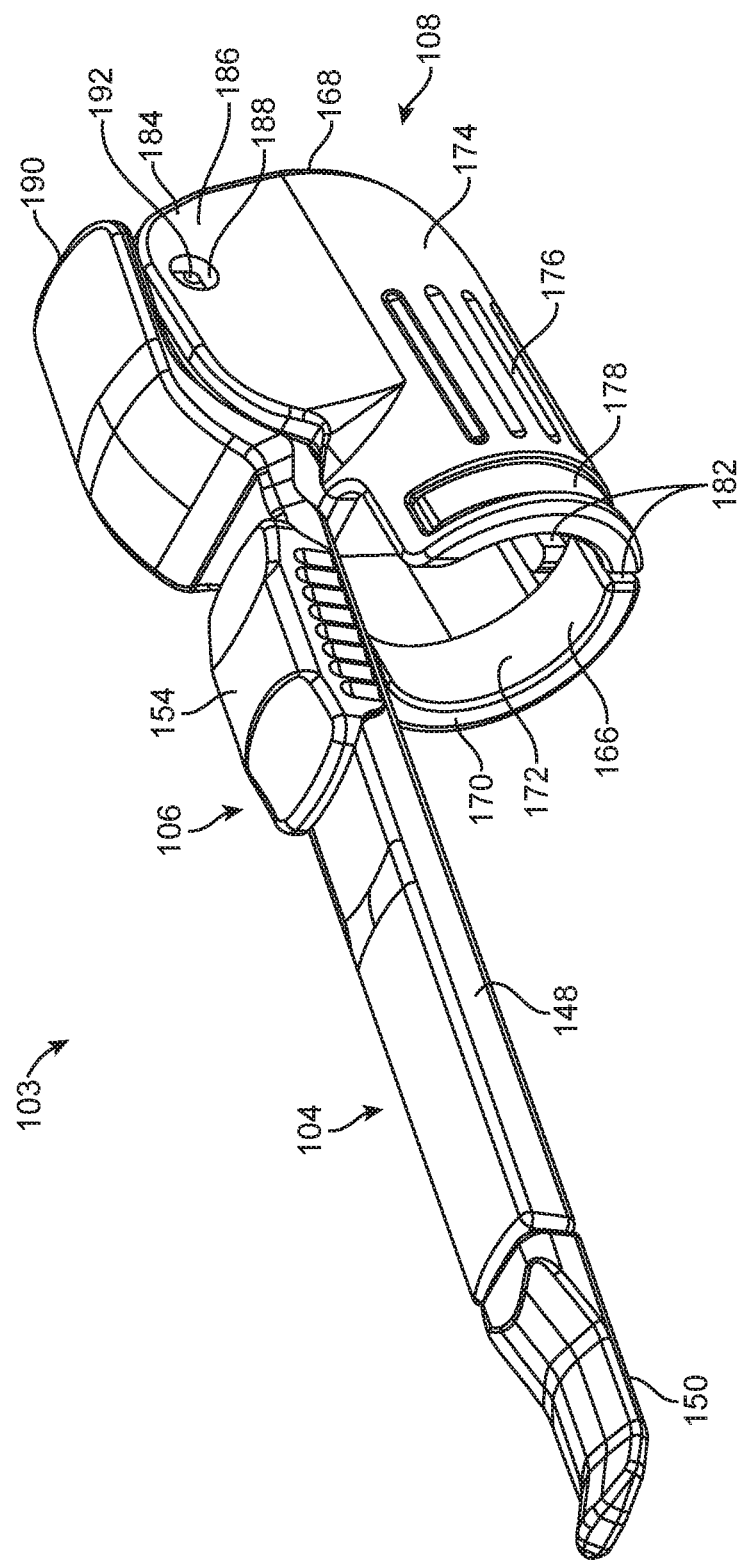
FIG. 4 is a perspective view of an actuator assembly used in the control of the surgical instrument illustrated in FIGS. 1 and 2.

With reference to the actuator assembly 103 of FIG. 4, the actuator assembly 103 includes the lever 104 mounted to the collar 108. The collar 108 is rotatably mounted to the housing as illustrated in FIGS. 1 and 2. The lever 104 includes an elongated base 148, and a terminal end 150. The terminal end 150 can be extendable from the elongated base 148. The terminal end 150 can be slidably extendable away from the elongated base 148. The elongated base 148 includes a switch mounting region 152. A switch body 154 can be pivotally mounted to the lever 104 at the switch mounting region 152.

With continued reference also to FIG. 2, the actuator 106 includes the switch body 154 and the magnet 142. The switch body 154 is moveably (e.g., slidably) coupled to the lever 104. The magnet 142 is included in the switch body 154. The switch body 154 includes an actuator holder 156 that houses the magnet 142 and provides a fastener passageway. The switch body 154 also includes an engagement member 158 that can be mated within the fastener passageway. The magnet 142 can be positioned in the actuator holder 156. The magnet 142 can be, for example, a samarium cobalt magnet, and/or a variety of other actuators know in the art. The switch body 154 is moveably coupled to the lever 104 by positioning the actuator holder 156 in the switch mount region 152 and positioning the engagement member 158 adjacent the top wall of the lever 104 such that bottom portion of the engagement member 158 extends through the switch mounting aperture defined by the lever 104. A fastener is then positioned in the fastener passageway defined by the actuator holder 156 and engaged with the fastener aperture defined by the engagement member 158 to couple the switch body 154 to the lever 104. With the switch body 154 coupled to the lever 104, the switch body 154 can be slidingly moveable relative to the lever 104 in the switch mounting region 152. The actuator 106 can be locked into an activated or an inactivated position.

The lever 104 is mounted to the collar 108 at a mounting section 160. The mounting section 160 includes an opening 162 at a bottom surface of the lever 104 to house a retaining member 164, such as a spring. The retaining member 164 couples to the lever 104 and to the collar 108 in order to pivotally connect the lever 104 to the collar 108. The lever 104 is coupled to the housing 102 with the collar 108. The collar 108 can be rotatably coupled to the housing 102, as described in more detail below. In some embodiments, the collar 108 is removable from the housing 102. In one embodiment, the collar 108, and is thus also the lever 104, is rotatable to any number of positions circumferentially around the housing 102. The collar 108 can be rotatably locked into a circumferential position with respect to the housing 102. A cylindrical base 166 of the collar 108 encircles the housing 102. The collar 108 can be removably mounted to the housing 102. In one embodiment, the collar is disposed proximal to the back nut 122 and the lever 104 extends away the back nut 122. The collar 108 includes the cylindrical base 166 having a front edge 168 and a rear edge 170 with an interior surface 172 and an exterior surface 174 extending between the front edge 168 and rear edge 170. A passageway is formed at the interior surface 172. In some embodiments, grooves 176 are formed along the exterior surface 174 for grasping by a user to facilitate rotating of the collar 108. In one embodiment, the grooves 176 extend parallel to the longitudinal axis 116.

As further illustrated in FIG. 4, the collar 108 can have holding ring indent 178 circumferentially disposed extending from the exterior surface 174 partially toward the interior surface 172. The holding ring indent 178 is configured to accommodate a holding ring 180 to temporarily lock the collar 108 unto the housing 102 (see, e.g., FIG. 1). The collar 108 includes a mounting channel 182 extending through the collar 108 from the interior surface 172 to the exterior surface 174. The mounting channel 182 can be segmented into circumferential and longitudinal portions. The mounting channel 182 is mateable with a nub (not shown) on the housing 102.

The collar 108 includes a lever mount 184. The lever mount 184 can include a channel defined between spaced apart mounting tabs that extend outwardly from the main body of the collar 108. The mounting tabs 186 can extend parallel with the longitudinal axis 116. The mounting tabs 186 can each include an aperture 188 for mounting the lever 104. The collar 108 includes spaced apart mounting tabs that extend outwardly from the main body of the collar 108. An end 190 of the lever 104 extends between the mounting tabs 186 and is connected by a pin 192 to the mounting tabs 186. A resilient member 164, such as a torsion spring, is located between the collar 108 and the lever 104 so that the lever 104 is normally pivoted away from the handpiece housing 102 in an "off", or inactivated, position.

In use, the actuator 106 is slidably moved by a user to a "run", or activated, positioned that is sensed by the sensor 134. The lever 104 is pivotably movable relative to the housing 102, and the sensor 134 maintained in the housing 102, in order to vary the magnetic field strength of the magnet 142 detected by the sensor 134 and to vary a signal produced by the sensor 134 in response to the magnetic field strength detected. The lever 104 can be pressed by a user to pivot the lever 104 toward the handpiece in a "run", or activated, position to adjust (i.e., increase or decrease) the rotational speed of the surgical implement attached to the instrument 100. The lever 104 can be maintained in any position along the range indicated by arrow 110 to maintain a desired rotational speed for a desired period of time. In one embodiment, the lever 104 when fully pivoted away from the housing is in the inactivated, or "off", position as detected by the sensor 134 and can be temporarily "locked" into the inactivated position.

Although the present disclosure has been described with reference to preferred embodiments, workers skilled in the art will recognize that changes can be made in form and detail without departing from the spirit and scope of the present disclosure.

What is claimed is:

1. A powered surgical instrument, comprising:
    a housing having a central longitudinal axis extending from a first end to a second end of the housing along a center of the housing;
    a printed circuit board having a first face and a second opposing face, the first and second faces extending perpendicularly to the central longitudinal axis;
    a sensor assembly including a first sensor coupled to the first face and a second sensor coupled to the second face, the first and second sensors disposed on and centered along the central longitudinal axis; and
    an actuator assembly including a lever and an actuator, the actuator assembly coupled to the housing to rotate about the central longitudinal axis with respect to the housing, the lever pivotally coupled to the housing, the lever maintaining an actuator slidably positionable along the lever, the actuator positionable to be proximal to the sensor, the actuator assembly including a magnet and operable to vary a magnetic field relative to the sensor assembly.

2. The powered surgical instrument of claim 1, wherein the lever is pivotable to extend parallel to the housing.

3. The powered surgical instrument of claim 1, wherein the lever and housing are configured to be grasped in a single hand of a user.

4. The powered surgical instrument of claim 1, wherein the actuator includes a magnet positioned within the lever and a switch body coupled to the magnet extends to an exterior of the lever and is slidable along the lever.

5. The powered surgical instrument of claim 1, wherein the first sensor and second sensor are Hall Effect sensors.

6. The powered surgical instrument of claim 4, wherein the magnet has a magnetic field axis oriented parallel to a length of the lever.

7. A control for a powered surgical instrument, the control comprising:
    a housing having a central longitudinal axis extending along a center of the housing from a first end of the housing to a second end of the housing;
    a pair of sensors mounted to a printed circuit board within the housing, each of the pair of sensors centrally disposed on the central longitudinal axis on an opposing surface of the printed circuit board; and
    an actuator assembly including a lever pivotally coupled to the housing and coupled to the housing to rotate about the central longitudinal axis with respect to the housing, the lever including a magnet, the lever operable to move the magnet relative to the pair of sensors in order in order to vary a signal that is produced by the pair of sensors in response to a magnetic field of the magnet.

8. The control of claim 7, wherein the lever is fully circumferentially rotatable around the central longitudinal axis of the housing.

9. The control of claim 7, wherein the pair of sensors are aligned to detect an axial component of a magnetic field of the magnet.

10. The control of claim 7, wherein the magnet is slidably positionable along a length of the lever.

11. The control of claim 7, wherein a magnetic field axis of the magnet is oriented along a length of the lever.

12. The control of claim 7, wherein the lever is removable from the housing.

* * * * *